(12) United States Patent
Yeh et al.

(10) Patent No.: US 11,344,400 B2
(45) Date of Patent: May 31, 2022

(54) IMPLANT DELIVERY ASSEMBLY WITH DISTAL PROTECTION FEATURE

(71) Applicants: STRYKER CORPORATION, Kalamazoo, MI (US); STRYKER EUROPEAN OPERATIONS LIMITED, County Cork (IE)

(72) Inventors: Vincent Yeh, Kalamazoo, MI (US); Miranda Ray, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 34 days.

(21) Appl. No.: 16/535,302

(22) Filed: Aug. 8, 2019

(65) Prior Publication Data

US 2021/0038362 A1 Feb. 11, 2021

(51) Int. Cl.
*A61F 2/01* (2006.01)
*A61F 2/95* (2013.01)

(52) U.S. Cl.
CPC ............. *A61F 2/013* (2013.01); *A61F 2/95* (2013.01); *A61F 2230/005* (2013.01)

(58) Field of Classification Search
CPC ........ A61F 2/013; A61F 2/014; A61F 2/9522; A61F 2/962; A61F 2002/015; A61F 2002/9505; A61F 2002/9665
See application file for complete search history.

(56) References Cited

U.S. PATENT DOCUMENTS

| | | | |
|---|---|---|---|
| 6,478,814 B2 | 11/2002 | Wang et al. | |
| 6,830,575 B2 | 12/2004 | Stenzel et al. | |
| 8,591,566 B2 | 11/2013 | Newell et al. | |
| 2005/0096724 A1* | 5/2005 | Stenzel | A61F 2/95 623/1.11 |
| 2007/0005122 A1 | 1/2007 | Inoue | |
| 2008/0140003 A1* | 6/2008 | Bei | A61M 25/10 604/103.05 |
| 2010/0057184 A1* | 3/2010 | Randolph | A61F 2/962 623/1.12 |
| 2014/0172067 A1 | 6/2014 | Brown et al. | |
| 2016/0220403 A1* | 8/2016 | Newell | A61F 2/82 |

OTHER PUBLICATIONS

PCT International Search Report and Written Opinion for International Appln. No. PCT/US2020/045008, Applicant Stryker Corporation, dated Nov. 4, 2020 (8 pages).

* cited by examiner

*Primary Examiner* — Erich G Herbermann
(74) *Attorney, Agent, or Firm* — Vista IP Law Group, LLP

(57) ABSTRACT

A delivery system for deploying a medical implant includes an elongate delivery wire assembly slidably disposed within a delivery catheter lumen, the delivery wire assembly having an implant loading region configured for seating the implant when the delivery wire assembly is constrained within the delivery catheter lumen and the implant is in a compressed delivery configuration, the delivery wire assembly further including an implant distal protection feature having a central portion coupled to the delivery wire assembly distal of the implant loading region, and a peripheral portion extending proximally from the central portion to at least partially cover a distal end portion of the implant when the delivery wire assembly, implant and implant distal protection feature are constrained within the delivery catheter lumen, wherein the peripheral portion remains extending in the proximal direction when the implant assumes an expanded configuration after being released from the delivery catheter lumen.

15 Claims, 5 Drawing Sheets

IMPLANT DELIVERY ASSEMBLY WITH DISTAL PROTECTION FEATURE

FIELD

The presently disclosed inventions relate generally to minimally invasive assemblies used for delivering medical implants. More particularly, the present disclosure relates to delivery assemblies for delivering medical implants, such as a tubular stent or flow diverter, to a targeted implantation site in the vasculature of a patient.

BACKGROUND

The use of intravascular implants, such as stents, stent grafts, flow-diverters, aneurysm occlusive devices, vena cava filters, etc., has become an effective method for treating many types of vascular disease. In general, a suitable intravascular implantable device is inserted into the vascular system of the patient and navigated through the vasculature to a targeted implantation site using a delivery system, such as a catheter having a delivery lumen. Using currently available delivery apparatus, virtually any target site in the patient's vascular system may be accessed, including the coronary, cerebral, and peripheral vasculature.

Minimally invasive delivery devices include catheters that are percutaneously introduced into the patient's vasculature over a guidewire, wherein an open distal end of the catheter is navigated to a targeted implantation site using well-known techniques. A medical implant is then deployed through a delivery lumen of the catheter in a compressed (i.e., reduced diameter) delivery configuration, and then introduced into a lumen of a blood vessel through the distal end opening of the catheter. For example, self-expanding implants, such as stents, are delivered in an elastically compressed state while being confined within the tubular catheter delivery lumen, and then elastically expand once deployed out the open distal end of the catheter and into engagement with the interior wall of the blood vessel. The expanded and enlarged stent supports and reinforces the vessel wall, thereby maintaining the vessel in an open and unobstructed condition.

Medical implants may have a variety of sizes and shapes. For example, stents and some flow-diverters usually assume an expanded, substantially tubular configuration when deployed within the vasculature of a patient. Further, medical implants can be made from a variety of materials, including polymers (e.g., nonbioerodable and bioerodable plastics) and metals. Medical implants can be made from shape memory or superelastic materials, such as shape memory metals (e.g., shape memory Nitinol) and polymers (e.g., polyurethane). Such shape memory implants can be induced (e.g., by temperature, electrical or magnetic field or light) to take on a shape (e.g., a radially expanded shape) after delivery to a treatment site. Superelastic embolic materials, such as superelastic Nitinol, take on a shape after delivery without the need for an inductive stimulus. Other commonly used materials include stainless steel, platinum and elgiloy. Drug delivery implants can carry, and/or the surface of the device, can be coated with bioactive or therapeutic agents. Commonly used medical implants, such as stents, stent grafts, flow-diverters, may be composed of a plurality of filaments (e.g., wires) that are braided or woven into predetermined (e.g., tubular) shape, or may be made out of laser cut tubes.

Known delivery systems may include retainer sleeves to control release or covers to protect the ends of the implants during deployment, which are illustrated and described (by way of example) in U.S. Pat. Nos. 6,478,814, 6,830,575 and 8,591,566. Such sleeves/covers include winged or separate members that may be more challenging to manufacture and may increase resistive or frictional forces imposed by the device assembly when being pushed through the delivery catheter, negatively impacting the overall performance of the delivery system.

Therefore, there is an ongoing need to provide an implant delivery system for delivering self-expanding implants that facilitates protection of the implant, while avoiding or minimizing an increase in resistive or frictional forces through the delivery catheter.

SUMMARY

In one embodiment of the disclosed inventions, a delivery system is provided for deploying an implant at a target site within a mammalian vasculature, the implant having a compressed delivery configuration and an expanded deployed configuration, wherein the delivery system includes an elongate delivery wire assembly at least partially disposed within the lumen of a delivery catheter, the delivery wire assembly being translatable relative to the delivery catheter, and having an implant loading region configured for seating the implant when a distal portion of the delivery wire assembly including the implant is constrained within the delivery catheter lumen and the implant is in the compressed delivery configuration. The delivery wire assembly includes an implant distal protection feature comprising a central portion coupled to the delivery wire assembly distal of the implant loading region, and a peripheral portion extending proximally from the central portion to at least partially cover a distal end portion of the implant when the distal portion of the delivery wire assembly, including the implant and implant distal protection feature, is constrained within the delivery catheter lumen, and wherein the peripheral portion of the implant distal protection feature remains extending in the proximal direction when the implant assumes the expanded configuration after being released from the delivery catheter lumen and is no longer covered by the implant distal protection feature.

In various embodiments, the peripheral portion of the implant distal protection feature may be comprised of a plurality of circumferentially spaced petal-like portions that extend from the central portion. By way of non-limiting example, in one embodiment, the peripheral portion of the implant distal protection feature consists of three petal-like portions that are substantially evenly circumferentially spaced around the delivery wire assembly.

In one embodiment, the implant distal protection feature covers about twenty percent of a total length of the implant when the distal portion of the delivery wire assembly including the implant and implant distal protection feature is constrained within the delivery catheter lumen.

In another embodiment, the implant distal protection feature covers between about ten percent and about twenty percent of a total length of the implant when the distal portion of the delivery wire assembly including the implant and implant distal protection feature is constrained within the delivery catheter lumen.

In yet another embodiment, the implant distal protection feature covers between about five percent and about ten percent of a total length of the implant when the distal portion of the delivery wire assembly including the implant and implant distal protection feature is constrained within the delivery catheter lumen.

In still another embodiment, the implant protection member covers about five percent or less of a total length of the implant when the distal portion of the delivery wire assembly including the implant and implant distal protection feature is constrained within the delivery catheter lumen.

The central portion of the implant distal protection feature may be fixedly attached to the delivery wire assembly in a manner such that the implant distal protection feature is not rotatable relative to the delivery wire assembly. In alternative embodiment, the central portion of the implant distal protection feature is attached to the delivery wire assembly in a manner such that the implant distal protection feature is rotatable relative to the delivery wire assembly.

Other and further aspects and features of embodiments of the herein disclosed inventions will become apparent from the ensuing detailed description in view of the accompanying figures.

DETAILED DESCRIPTION OF THE ILLUSTRATED EMBODIMENTS

Figure 1:
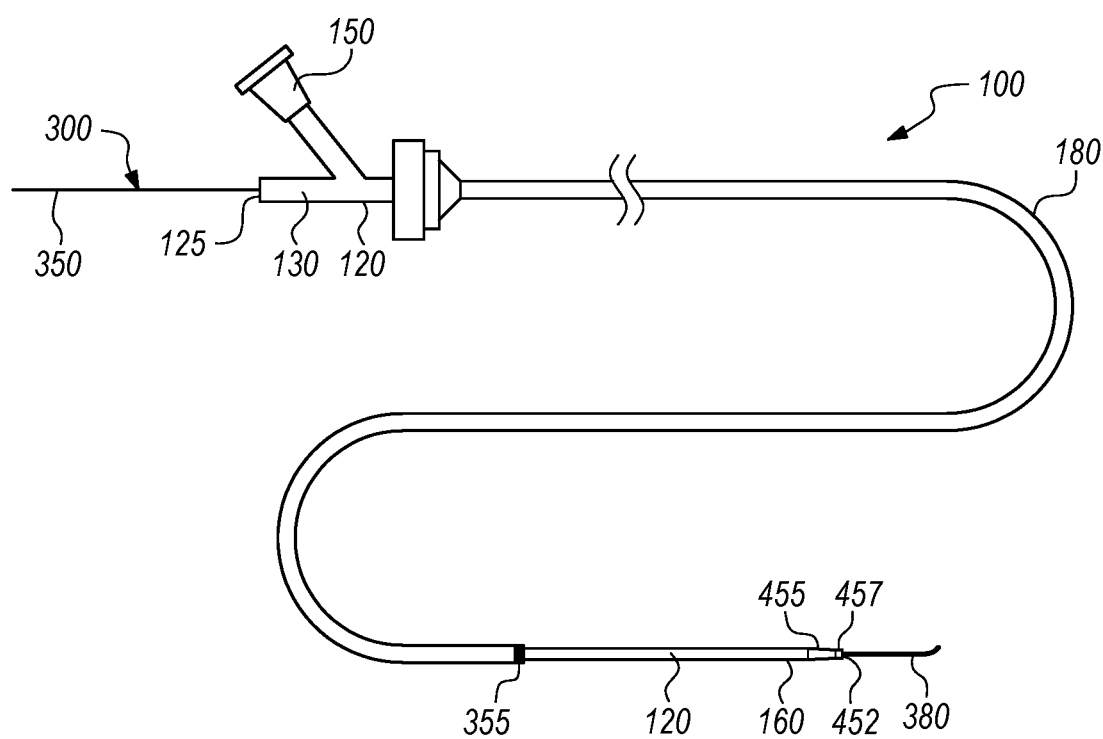
FIG. 1 is a side view of an implant delivery system constructed according to one embodiment of the disclosed inventions.

For the following defined terms, these definitions shall be applied, unless a different definition is given in the claims or elsewhere in this specification.

All numeric values are herein assumed to be modified by the terms "substantially" or "about," whether or not explicitly indicated. The terms "substantially" and "about" refer to a range of numbers that one of skill in the art would consider equivalent to the recited parameter, structure or value (i.e., having the same function or result). In many instances, the terms "about" and "substantially" include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the terms "proximal" and "proximally" (and the like) when used to describe a relative position, the location or direction of a structure or action of the implant delivery system that is towards the outside of the patient's body; and the terms "distal" and "distally" (and the like) when used to describe a relative position, the location or direction of a structure or action of the implant delivery system that is extended deepest into the patient's body.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the disclosed inventions, or as a limitation on the scope thereof, which is defined only by the appended claims and their equivalents.

In addition, the respective illustrated embodiments of the disclosed inventions need not have all of the depicted features, and a feature, aspect or advantage described in conjunction with a particular embodiment is not necessarily limited to that embodiment, but can be practiced in other embodiments, even if not so illustrated.

FIG. 1 illustrates an implant delivery system 100, constructed according to the one embodiment of the disclosed inventions. The implant delivery system 100 generally comprises an elongate, tubular delivery catheter 120 having a proximal end portion 130, a distal end portion 160, and a lumen 125 extending there between, wherein the delivery catheter lumen 125 is in communication with respective open proximal and distal ends of the delivery catheter 120. The delivery catheter 120 is coaxially disposed within, and movable relative to, an outer sheath 180 that is used to help position the distal end portion 160 of the delivery catheter 120 within a target portion of the vasculature. The proximal end portion 130 of the delivery catheter 120 includes a fluid port 150 (distal to a proximal opening in the outer sheath 180 through which the delivery catheter 120 is inserted) used to introduce fluids into the lumen 125. The fluid delivery port 150 remains outside of the patient's body so as to be accessible to the physician/operator when the implant delivery system 100 is inserted into a patient's vasculature. The distal portion 160 of the delivery catheter 120 is sized and dimensioned to access remote locations within the vasculature, such as, e.g., within the neuro-vasculature. And may have a smaller diameter (or profile) than the proximal portion 130.

The implant delivery system 100 further includes an implant delivery wire assembly 300 (described below in greater detail in conjunction with FIGS. 2A-E), including a core wire 350 that is pushed through the delivery catheter lumen 125 for delivering an implant 200 (not shown in FIG. 1) carried on a distal end portion of the core wire 350 to a targeted site in a patient's vasculature. As depicted in FIG. 1, the core wire 350 has been inserted through the proximal end opening of the delivery catheter 120, and pushed through the delivery lumen 125, such that an atraumatic distal tip portion (e.g., a soft coil member) 380 attached to a distal end of the core wire 350 is extending out a distal end opening of the delivery catheter 120.

The outer sheath 180 of the implant delivery system 100 may be introduced into the vasculature over a guidewire (not shown) that has been previously introduced, known as an over-the-wire configuration), or alternatively may be introduced in a "rapid-exchange" configuration, where a guidewire extends through only a distal portion of the outer sheath 180 from a guidewire port (not shown), as is well-known. The delivery catheter 120 is then introduced through the outer sheath, whether over the guidewire or otherwise, again, as is well-known. The outer sheath 180 includes a radiopaque marker 355 adjacent to an open distal end of the sheath to assist with positioning thereof in a targeted location of the vasculature.

Figure 2:
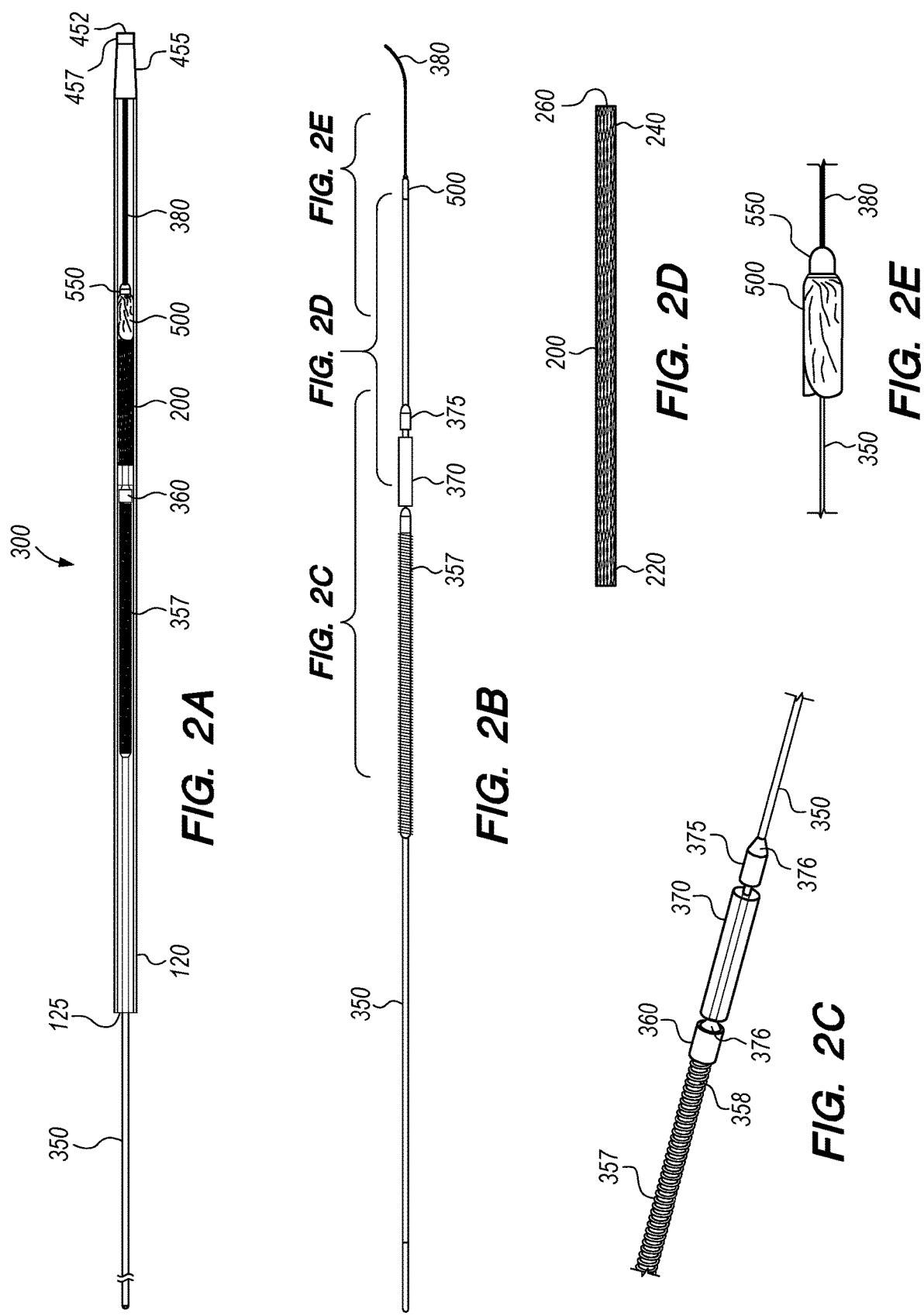
FIGS. 2A-E are partially cut-away side, perspective and exploded views of a delivery wire assembly of the implant delivery system of FIG. 1, showing portions of the system in greater detail including an implant distal protection feature.

The delivery catheter 120 may be composed of suitable polymeric materials, metals and/or alloys, such as polyethylene, stainless steel or other suitable biocompatible materials or combinations thereof. In some instances, the proximal portion 130 may include a reinforcement layer, such a braided layer or coiled layer to enhance pushability. The delivery catheter 120 may include one or more transition regions between the proximal portion 130 and the distal portion 160. The distal end portion 160 may have an outer diameter less than the outer diameter of the proximal portion 130 in order to reduce the profile of the distal end portion 160, and facilitate navigation of the distal end portion 160 extending out the distal opening of the outer sheath 180 in tortuous vasculature. The proximal end portion 130 may be formed from material that is stiffer than the distal portion 160 of the delivery catheter 120, so that the proximal portion 130 has sufficient pushability to advance through the patient's vascular system, while the distal portion 160 may be formed of a more flexible material so that the distal portion 160 may remain flexible and track more easily over a guidewire to access remote locations in tortuous regions of the vasculature. As best seen in FIG. 2A, a tapered radiopaque marker 455, and atraumatic tip 457, respectively, are disposed proximate a distal end opening 452 of the delivery catheter 120.

Referring to FIGS. 2A-E, the implant 200, which may be a stent, a flow diverter, or other type of vasculature implant, is carried on a distal portion of the core wire 350. The implant 200 may comprise a variety of biocompatible materials, such as stainless steel, elgiloy, nickel, titanium, nitinol, shape memory polymers, or combinations thereof, and may be constructed using well-known techniques, such as by etching or cutting a pattern from a tube or sheet of stent material, or by weaving/braiding one or more wires or ribbons into a desired shape and pattern. The implant 200 may include further components that are welded, bonded or otherwise engaged to one another, and may optionally include a non-porous, non-permeable biocompatible material, cover or the like.

As best seen in FIG. 2D, the implant 200 is generally tubular, and has a proximal portion 220, a distal portion 240, and an inner lumen 260 extending therebetween. Notably, the implant 200 is depicted in FIGS. 2A-E in a compressed, elongated delivery configuration disposed (i.e., radially constrained) within the lumen 125 of the delivery catheter 120. The implant 200 is preferably biased to self-expand radially outwards into an expanded deployed configuration when deployed out the distal end opening of (i.e., no longer radially constrained within) the delivery catheter 120.

As shown in FIGS. 2A-B, the core wire 350 of the delivery wire assembly 300 is coaxially disposed within the delivery catheter lumen 125, and the implant 200 is coaxially disposed around the core wire 350, also constrained within the delivery catheter lumen 125. In particular, the core wire 350 is axially movable relative to the delivery catheter 120, with the delivery wire assembly 300 being configured to engage the implant 200 as the core wire 350 is axially translated through the delivery catheter lumen 125 for delivery of the implant 200 at a targeted implantation site in a vasculature. The interface between the delivery wire assembly 300 and the implant 200 is described in further detail below.

Radiopaque markers 360 (e.g., laser etched, radiopaque bands or any other suitable markers) are preferably located along the distal portion of the core wire 350 to assist in positioning the core wire 350 and implant 200 relative to the delivery catheter 120. In the illustrated embodiment, a coil 357 is disposed around the core wire 350 for providing structural support just proximal of the implant 200. A radiopaque marker band 360 is disposed on a distal portion 358 of the coil 357 to indicate the location of the proximal end portion 220 of the implant 200. An epoxy bond 376 is used to attach the marker 360 to the core wire 350.

As shown in FIGS. 2B-C, a re-sheathing pad 370 is disposed around the core wire 350 distal of the coil 357, and an implant re-sheathing bumper 375 is attached to the core wire 350 at the distal end of the re-sheathing pad 370. An epoxy bond 376 is used to attach the re-sheathing bumper to the core wire 350. This region of the core wire 350 onto which the implant 200 is loaded is referred to herein as the implant loading region. In particular, the proximal portion 220 of the implant 200 is disposed over the respective re-sheathing pad 370 and re-sheathing bumper 375, and a distal end of the distal portion 240 of the implant 200 is covered by a distal protection feature 500 (FIG. 2E) that is attached to the core wire 350 and secured between respective proximal and distal locking members 550. In most of the figures, the only the distal locking member 550 is shown, as the proximal locking member 550 is obscured by the implant distal protection feature 500. However, the proximal locking member is shown in FIG. 5C (described below). The atraumatic distal tip 380 (e.g., a soft coil member) is attached to the core wire proximate to the distal locking member 550 (FIGS. 2B, 2E).

Figure 3:
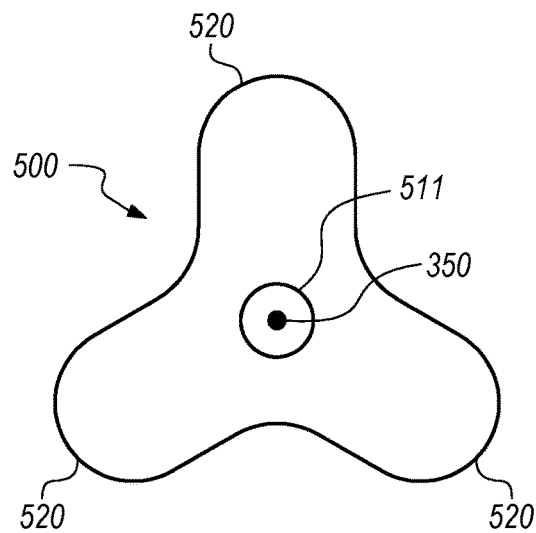
FIG. 3 is elevated end view of the implant distal protection feature shown in FIG. 2E, wherein the implant distal protection feature is fully opened.
Figure 4A:
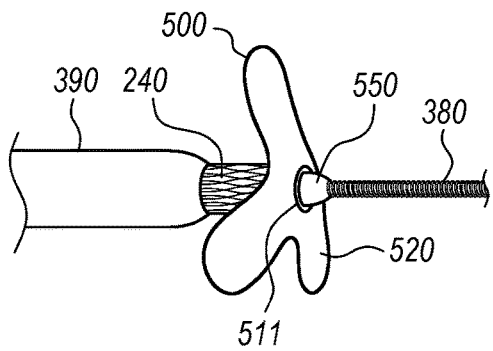
FIGS. 4A-D are cut-away, side and perspective views of the implant distal protection feature depicted as the delivery wire assembly is loaded into the delivery catheter 120, according to one embodiment of the disclosed inventions.

FIG. 3 illustrates the implant distal protection feature 500 of the delivery wire assembly 300, according to one embodiment of the disclosed inventions. The implant distal protection feature 500 is preferably composed of biocompatible material, such as ePTFE or the like. In one embodiment, the implant distal protection feature 500 is made of a thin, substantially uniform layer of ePTFE, having a thickness of approximately 0.0152 millimeters (0.0006 inches), and a length L of approximately 0.44 millimeters (0.0173 inches). As shown in FIG. 3, the implant distal protection feature 500 comprises a peripheral portion in the form of three circumferentially spaced apart petal-like members (or "petals") 520 that meet at a central portion 511 that is attached to the core wire 350 (FIG. 2E). As shown in FIG. 4A (described below), the peripheral petals 520 extend generally radially outward from the central portion 511, and proximally directed, when the implant distal protection feature 500 is not constrained within the delivery catheter 120.

In the illustrated embodiment, the implant distal protection feature 500 is fixedly attached to the core wire 350 by the locking members 550, so that the implant distal protection feature does not rotate relative to the core wire 350. In an alternative embodiment, the implant distal protection feature 500 may be attached to a collar (not shown) that is still fixed in a relative longitudinal position on the core wire 350 by the locking members 550 in a manner that allows the collar, and thus the implant distal protection feature 550, to rotate relative to the core wire 350 and locking members 550.

FIGS. 4A-D illustrate the front loading of the delivery wire assembly 300 into the delivery catheter 120, according to one embodiment of the disclosed inventions. FIG. 4A depicts the distal end portion of the delivery wire assembly 300, including the implant distal protection feature 500 and implant 200, just prior to being loaded into the delivery catheter 120, wherein the peripheral petals 520 of the implant distal protection feature 500 are shown extending generally proximally in a radially unconstrained configuration. The implant 200 is coaxially disposed around the core wire 350 (not shown), and held in the radially constrained delivery configuration by a tubular loading member 390, with the distal end portion 240 of the implant 200 is at least partially exposed out a distal end opening of the loading member 390.

Figure 4B:
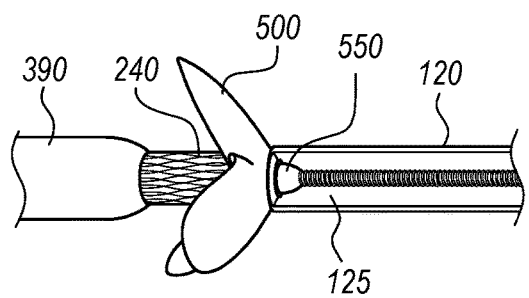
Figure 4C:
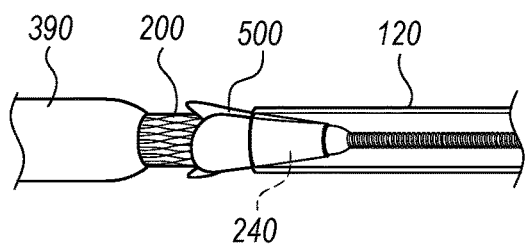
Figure 4D:
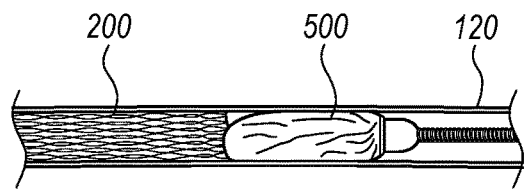

The distal end portion of the delivery wire assembly 300, including the implant distal protection feature 500 and the compressed implant 200, is either advanced into the delivery catheter 120, or the delivery catheter 120 is advanced over the distal portion of the delivery wire assembly 300, or some of each, thereby radially compressing the peripheral petals 520 of the implant distal protection feature 500 over and onto the distal portion 240 of the implant 200, as shown in FIGS. 4B-C. Once the delivery catheter 120 is disposed over the respective implant distal protection feature 500 and loading member 390, the loading member 390 is withdrawn, while the implant 200 remains in the compressed delivery configuration within the lumen 125 of the delivery catheter 120, and the peripheral petals 520 of the implant distal protection feature 500 remain compressed onto, and at least partially covering, the distal portion 240 of the implant 200 (FIG. 4D).

Although the disclosed inventions are not so limited, the illustrated "three-petal" configuration of the implant distal protection feature 500 is configured to minimize the amount of material covering the distal end of the distal portion 240 of the implant 200, thereby reducing and minimizing resistive or frictional forces imparted by the implant on the inner wall of the delivery catheter 120 as the implant 200 is pushed through the lumen 125. In particular, the inventor(s) of the disclosed inventions have found that, by employing the depicted three-petal configuration of the implant distal protection feature 500, the coefficient of friction between the implant 200 and the inner wall of the delivery catheter 120 ranges from approximately 0.01 to approximately 0.04 when there is relative motion between the core wire 350 and the delivery catheter 120.

In various embodiments, the implant distal protection feature 550 may be sized and configured to cover differing amounts of the distal end portion 240 of the implant 200 when a distal portion of the delivery wire assembly 300 including the implant 200 and implant distal protection feature 500 is constrained within the delivery catheter lumen 125. By way of non-limiting examples, in one embodiment, the implant distal protection feature 500 is sized and configured to cover as much as about twenty percent of a total length of the implant 200 when a distal portion of the delivery wire assembly 300 including the implant 200 and implant distal protection feature 500 is constrained within the delivery catheter lumen 125. In another embodiment, the implant distal protection feature 500 is sized and configured to cover between about ten percent and about twenty percent of a total length of the implant 200 when a distal portion of the delivery wire assembly 300 including the implant 200 and implant distal protection feature 500 is constrained within the delivery catheter lumen 125. In still another embodiment, the implant distal protection feature 500 is sized and configured to cover between about five percent and about ten percent of a total length of the implant 200 when a distal portion of the delivery wire assembly 300 including the implant 200 and implant distal protection feature 500 is constrained within the delivery catheter lumen 125. In yet another embodiment, the implant distal protection feature 500 is sized and configured to cover about five percent or less of a total length of the implant 200 when a distal portion of the delivery wire assembly 300 including the implant 200 and implant distal protection feature 500 is constrained within the delivery catheter lumen 125.

FIGS. 5A-D' illustrate the implant distal protection feature 500 during delivery and deployment of the implant 200 to/at a targeted site in a vasculature (not shown).

Figure 5A:
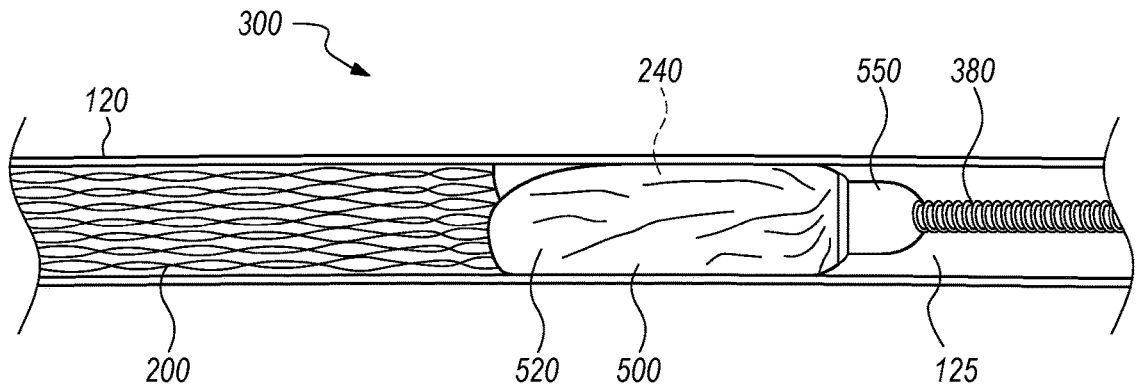
FIGS. 5A-D' are side and perspective views of the implant distal protection feature depicted during delivery and deployment of an implant at a targeted site in a vasculature using the implant delivery system of FIGS. 1-4.

FIG. 5A, depicts a distal end portion of the delivery wire assembly 300 as the core wire 350 (not seen in FIG. 5A) is pushed through the delivery catheter lumen 125. The implant 200 and distal implant protection member 500 shown in the compressed delivery configuration, constrained within the delivery catheter lumen 125, with the peripheral petals 520 of implant distal protection feature 500 covering and protecting the distal portion 240 of the implant 200

Figure 5B:
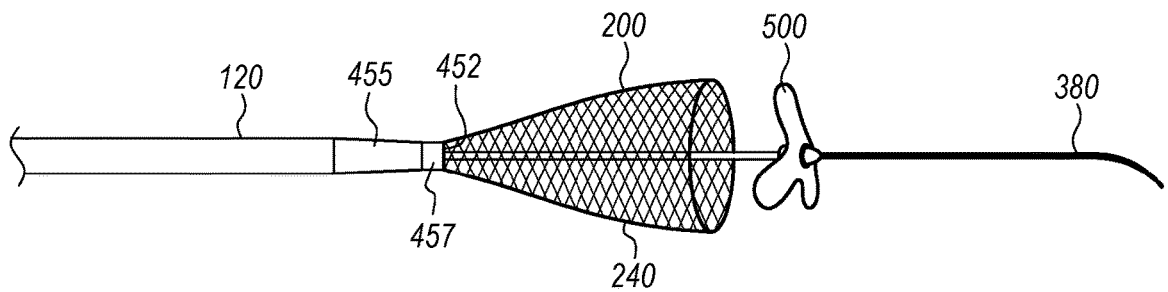
Figure 5C:
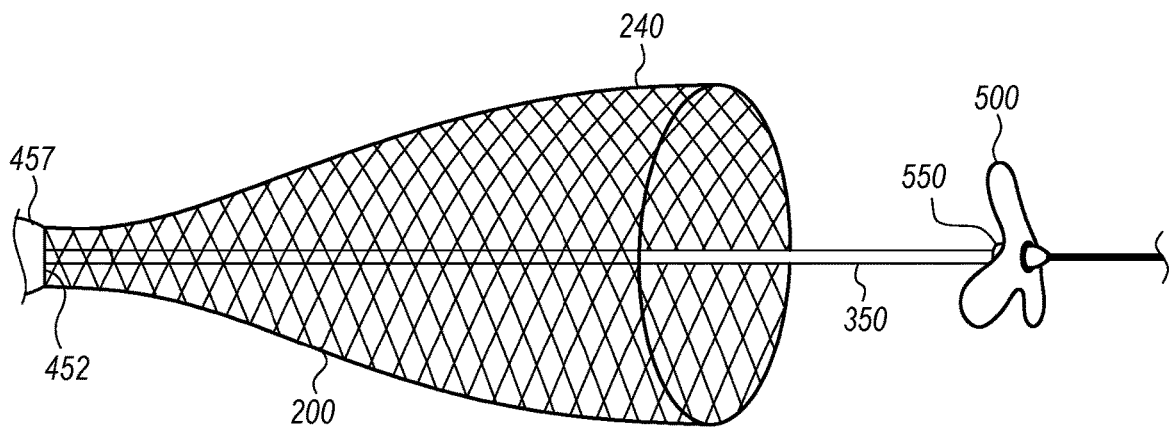
Figure 5D:
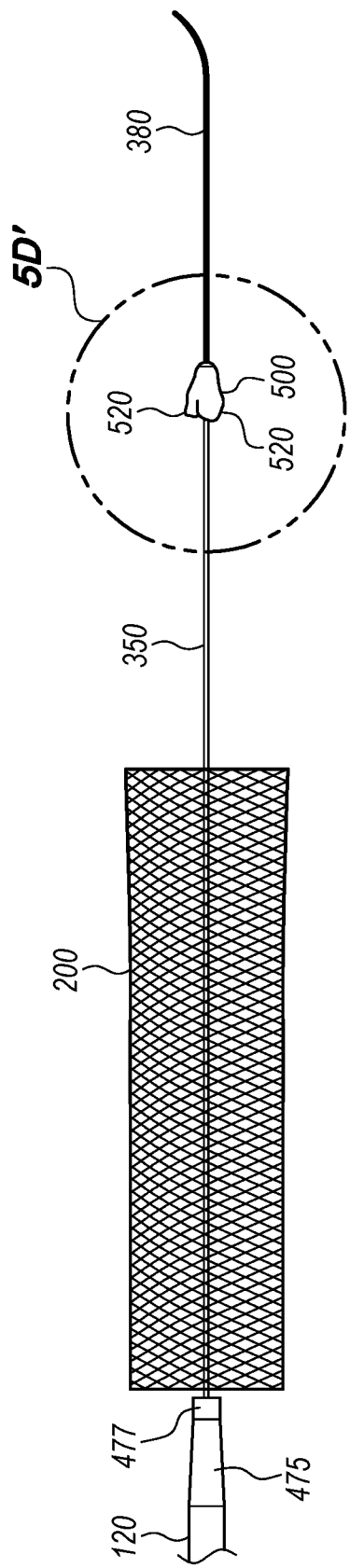
Figure 5D:
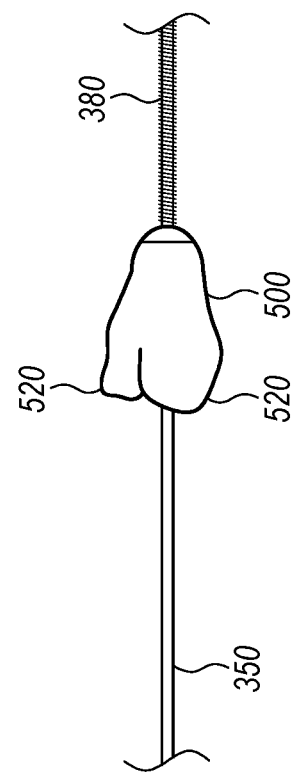

Once the distal end portion of the delivery assembly 300 is located proximate to the targeted implantation site, the delivery catheter 120 is withdrawn proximally relative to the core wire 350, or the core wire 350 is pushed distally relative to the delivery catheter 120, or some of each, thereby exposing the implant distal protection feature 500 and the implant 200 out the distal end opening 452 of the delivery catheter 120, allowing the no-longer radially constrained implant 200 to self-expand radially, starting at the distal end portion 240, to the expanded configuration, as shown in FIGS. 5B-5D'. Notably, the peripheral petals 520 of the implant distal protection feature 500 remain generally extending in the proximal direction (i.e., in the "delivery configuration") as the distal end portion 240 of the implant 200 assumes the expanded configuration and is no longer covered by the implant distal protection feature 500.

The implant distal protection feature 500 is preferably configured to exert negligible or otherwise insignificant forces over the distal portion 240 of the implant 200 as the implant 200 expands. In some embodiments, the implant distal protection feature 500 may outwardly radially expand when no longer radially constrained by the delivery catheter 120. In either embodiment, when the implant distal protection feature 500 retains the delivery configuration or outwardly expands when no longer constrained by the delivery catheter 120, the peripheral petals 520 are configured to extend and/or face in a proximal direction, i.e., the individual petals 520 preferably do not evert as the implant 200 expands.

After deployment of the implant 200 at the targeted site, the delivery wire assembly 300 is withdrawn back into the delivery catheter (not shown), and the delivery system 100 is withdrawn from the body, leaving the expanded implant 200 implanted at the targeted site. Notably, the core wire 350 and distal implant protection member 500 are pulled through the lumen 260 of the implant 200 and back into the delivery catheter lumen 125 without interfering with the deployed expanded implant 200, due to the implant distal protection feature 500 "proximal facing" configuration and its relatively small size with respect to the expanded implant 200, as shown in FIG. 5D-5D'. FIG. 5D' is an enlarged view of the section shown in FIG. 5D, to better illustrate that the implant distal protection feature 500 substantially retains its delivery configuration even when the delivery catheter 120 is no longer constraining the implant distal protection feature 500.

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A delivery system for deploying an implant at a target site within a mammalian vasculature, the implant having a compressed delivery configuration and an expanded deployed configuration, the delivery system comprising: a delivery catheter having a lumen; an elongate delivery wire assembly at least partially disposed within the delivery catheter lumen, the delivery wire assembly being translatable relative to the delivery catheter and having an implant loading region configured for seating the implant when a distal portion of the delivery wire assembly including the implant is constrained within the delivery catheter lumen and the implant is in the compressed delivery configuration; and an implant distal protection feature comprising a central portion coupled to the delivery wire assembly distal of the implant loading region, and a peripheral portion extending proximally from the central portion to at least partially cover a distal end portion of the implant when the distal portion of the delivery wire assembly including the implant and implant distal protection feature is constrained within the delivery catheter lumen, wherein the peripheral portion of the implant distal protection feature is configured to expand when the peripheral portion of the implant distal protection feature is no longer constrained by the delivery catheter, and the peripheral portion of the implant distal protection feature is configured to not evert from a proximally facing direction to a distally facing direction so that the peripheral portion of the implant distal protection feature remains extending in the proximally facing direction when the implant assumes the expanded deployed configuration after the implant has been released from the delivery catheter lumen and is no longer covered by the peripheral portion of the implant distal protection feature, and wherein the peripheral portion of the implant distal protection feature comprises a plurality of circumferentially spaced petal-like portions that extend from the central portion.

2. The delivery system of claim 1, wherein the peripheral portion of the implant distal protection feature consists of three petal-like portions.

3. The delivery system of claim 1, wherein the petal-like portions are substantially evenly circumferentially spaced around the delivery wire assembly.

4. The delivery system of claim 1, wherein the implant distal protection feature covers about twenty percent of a total length of the implant when the distal portion of the delivery wire assembly including the implant and implant distal protection feature is constrained within the delivery catheter lumen.

5. The delivery system of claim 1, wherein the implant distal protection feature covers between about ten percent and about twenty percent of a total length of the implant when the distal portion of the delivery wire assembly including the implant and implant distal protection feature is constrained within the delivery catheter lumen.

6. The delivery system of claim 1, wherein the implant distal protection feature covers between about five percent and about ten percent of a total length of the implant when the distal portion of the delivery wire assembly including the implant and implant distal protection feature is constrained within the delivery catheter lumen.

7. The delivery system of claim 1, wherein the implant distal protection feature covers about five percent or less of a total length of the implant when the distal portion of the delivery wire assembly including the implant and implant distal protection feature is constrained within the delivery catheter lumen.

8. The delivery system of claim 1, wherein the central portion of the implant distal protection feature is fixedly attached to the delivery wire assembly in a manner such that the implant distal protection feature is not rotatable relative to the delivery wire assembly.

9. The delivery system of claim 1, wherein the central portion of the implant distal protection feature is attached to the delivery wire assembly in a manner such that the implant distal protection feature is rotatable relative to the delivery wire assembly.

10. The delivery system of claim 1, wherein the implant distal protection feature is configured to exert negligible or insignificant forces over the distal portion of the implant as the implant expands from the compressed delivery configuration to the expanded deployed configuration.

11. The delivery system of claim 1, wherein the implant distal protection feature substantially retains a compressed delivery configuration after the implant distal protection feature radially expands and is no longer constrained by the delivery catheter.

12. The delivery system of claim 1, wherein the implant distal protection feature is configured to not evert to the distally facing direction as the implant expands.

13. The delivery system of claim 1, wherein the implant distal protection feature is configured to be withdrawn back into the delivery catheter without everting from the proximally facing direction to the distally facing direction.

14. The delivery system of claim 1, wherein the implant distal protection feature comprises a biocompatible material having a thickness of about 0.0006", a length of about 0.0173".

15. The delivery system of claim 14, wherein the peripheral portion of the implant distal protection feature consists of three petal-like portions that are circumferentially spaced around and extend from the central portion.

* * * * *